United States Patent [19]

Paulik

[11] Patent Number: 5,844,028
[45] Date of Patent: Dec. 1, 1998

[54] CYCLIC PHOSPHORUS CONTAINING FLAME RETARDANT COMPOUNDS

[75] Inventor: Frank E. Paulik, St. Louis, Mo.

[73] Assignee: Solutia Inc., St. Louis, Mo.

[21] Appl. No.: 961,278

[22] Filed: Oct. 30, 1997

Related U.S. Application Data

[63] Continuation of Ser. No. 963,537, Oct. 20, 1992, abandoned.

[51] Int. Cl.$^6$ .............................. C08K 5/49; C07F 9/02
[52] U.S. Cl. .............................. 524/117; 524/118; 521/85; 558/77; 558/83
[58] Field of Search .................. 558/77, 83; 521/85; 524/117, 118

[56] References Cited

U.S. PATENT DOCUMENTS

| | | | |
|---|---|---|---|
| 2,328,358 | 8/1943 | Pikl | 260/500 |
| 3,332,893 | 7/1967 | Birum et al. | 260/2.5 |
| 3,922,323 | 11/1975 | Reese et al. | 260/927 |
| 3,969,437 | 7/1976 | Shim | 558/83 |
| 4,034,141 | 7/1977 | Duffy et al. | 558/77 |
| 4,071,583 | 1/1978 | Hochenbleikner | 260/927 R |
| 4,073,767 | 2/1978 | Birum | 260/45.8 R |
| 4,139,476 | 2/1979 | Hancock | 252/8.1 |
| 4,351,779 | 9/1982 | Maier | 558/166 |
| 4,397,759 | 8/1983 | Hancock | 252/609 |
| 5,099,056 | 3/1992 | Ha et al. | 558/166 |

FOREIGN PATENT DOCUMENTS

| | | | |
|---|---|---|---|
| 50-24395 | 6/1975 | Japan . | |
| 390101 | 7/1973 | U.S.S.R. | 558/83 |
| 1045892 | 10/1966 | United Kingdom | 558/166 |

OTHER PUBLICATIONS

"Structure of Phosphorus Derivatives Containing A 1,3, 2–Dioxaphospholane Ring" Ovchinnikov et al., Zhurnal Obshchei Khimii, vol. 48, No. 11, pp. 2424–2423, Nov., 1978.

"Synthesis of Cyclic Phosphorous Acid Esters By Transesterification", A.A. Oswald, Can. J. Chem., vol. 37 (1959) pp. 1498–1504.

"Cyclic Organophosphorous Compounds I. Synthesis and Infrared Spectral Studies of Cyclic Hydrogen Phosphites and Thiophosphites", A. Zwierzak, Can. J. Chem., vol. 45 (1967) pp. 2501–2512 Apr. 25, 1967.

"Synthesis of Trimethylene Hydrogen Phosphites" Nifant'ev et al. Zhurnal Obshchei Khimii, vol. 41, No. 11, pp. 2368–2371, Nov., 1971.

"Ein Neues Verfahren Zer Darstellung Von Aminomethylenphosphonsäuren" Krüger et al., Chemiker–Zeitung, 96, Jahrgang (1972), NR. 12, pp. 691 Nov. 9, 1972.

"The Direct Synthesis of α–Aminomethylphosphonic Acids. Mannich–Type Reactions with Orthophosphorous Acid" Moedritzer et al., J. Org. Chem. 31, May 1966, pp. 1603–1607.

"Synthesis of Aminodiphosphonates and Aminotriphosphonates" Petrov et al., J. Gen. Chem. USSR, 29, 1959, English translation pp. 587–560.

Abstract, Mitsui Toatsu Chem., Inc., Jun. 29, 1973, Non–flammable Polyurethane Comp. (JP 50–24395).

"The Synthesis of Esters of Substituted Amino Phosphonic Acids", by Ellis K. Fields, Journal of the American Chemical Society, Mar. 20, 1952, vol. 74, No. 6, pp. 1528–1531.

Hackh's Chemical Dictionary, Fourth Edition, Completely Revised and Edited by Julius Grant, ©1969, p. 643.

"Synthesis of Aminodiphosphonates and Aminotriphosphonates", Petrov, et al., J. Gen. Chem. USSR, 29, 1959, pp. 587–560. (See Akademiia NAUK SSSR Leningrad Doklady, Novain Serila 1953, U. of Md).

English abstract of "Synthesis of Aminodiphosphonates and Aminotriphosphonates", Petrov, et al., J. Gen. Chem. USSR, 29, 1959, pp. 587–560. (See Akademiia NAUK SSSR Leningrad Doklady, Novain Serila 1953, U. of Md), reported in Chemical Abstracts, vol. 49, p. 840.

*Primary Examiner*—Kriellion S. Morgan
*Attorney, Agent, or Firm*—Fitzpatrick, Cella, Harper & Scinto

[57] ABSTRACT

Certain (1,3,2-dioxaphosphorinanemethan) amine compounds, which are useful as flame retardant compounds, are disclosed. The compounds are particularly useful in polyurethane compositions.

16 Claims, No Drawings

CYCLIC PHOSPHORUS CONTAINING FLAME RETARDANT COMPOUNDS

This application is a continuation of application Ser. No. 07/963,537 filed Oct. 20, 1992, abandoned.

BACKGROUND OF THE INVENTION

This invention relates to novel cyclic phosphorus-containing compounds and, in particular, to certain (1,3,2-dioxaphosphorinanemethan) amine compounds which are useful as fire retardant materials. The invention also relates to the use of the novel compounds as fire retardant materials.

Cyclic phosphorus compounds including dioxaphosphorinanes are known to be effective flame retardant compounds for various synthetic resin compositions. U.S. Pat. No. 4,073,767, to Birum, discloses cyclic phosphorus compounds which include phosphorinane rings which are taught to be useful as flame retardants for polyurethanes, polyesters and polyamides. In U.S. Pat. No. 4,397,750, to Hancock, certain cyclic phosphonate esters are shown to be useful flame retardants for polypropylene and other polyolefins.

This invention is directed to certain (1,3,2-dioxaphosphorinanemethan) amine compounds which are novel compositions and which are particularly useful as flame retardant materials for use in organic polymeric materials such as polyurethane foams, other compositions containing polyurethane and compositions containing polyesters, styrenic polymers, polyvinyl chloride, polyvinyl acetates or polycarbonates. These novel cyclic phosphorus compounds are of particular advantage over the prior art in that improved flame retardant characteristics such as low smoke and low smoulder are provided and, when they are used in foams, the compounds increase the load bearing capabilities of the foams.

SUMMARY OF THE INVENTION

The general formula for the novel (1,3,2-dioxaphosphorinanemethan) amine compounds of the invention is:

$A_{3-Y}$—N—$B_Y$ wherein A is

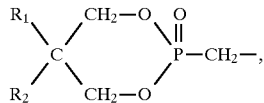

$R_1$ and $R_2$ are independently selected from the group consisting of hydrogen, halogen, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms, Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms.

The invention also provides a process for the preparation of the novel (1,3,2-dioxaphosphorinanemethan) amine compounds comprising the steps of:

(a) adding phosphorus trichloride to a mixture of a 1,3-diol derivative and water and an organic solvent at a temperature of from about 10° C. to about 60° C. to produce a 5,5-di-substituted 1,3,2-dioxaphosphorinane-2-oxide having the general formula:

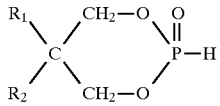

wherein $R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms;

(b) purifying the 5,5-di-substituted 1,3,2-dioxaphosphorinane-2-oxide;

(c) reacting the 5,5-di-substituted 1,3,2-dioxaphosphorinane-2-oxide, paraformaldehyde and an amine having the general formula:

$B_Y NH_{3-Y}$, wherein Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms, in an organic solvent to produce a (1,3,2-dioxaphosphorinanemethan) amine compound having the general formula:

$A_{3-Y}$—N—$B_Y$ wherein A is

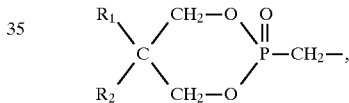

$R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms, Y is 1 or 2 and each B is independantly selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms; and (d) purifying and drying the (1,3,2-dioxaphosphorinanemethan) amine compound.

Organic polymeric compositions containing the (1,3,2-dioxaphosphorinanemethan) amine compounds of the invention which have improved fire retardant properties are also provided.

DESCRIPTION OF THE PREFERRED EMBODIMENTS

The novel (1,3,2-dioxaphosphorinanemethan) amine compounds of the invention which are shown by the above general formula include 1,3,2-Dioxaphosphorinane-2-methanamine, N-butyl-N-[(5,5-dimethyl-1,3,2-dioxaphosphorinan-2-yl)methyl]-5,5-dimethyl-, P,2-dioxide; 1,3,2-Dioxaphosphorinane-2-methanamine, N-[(5, 5-dimethyl-1,3,2-dioxaphosphorinan-2-yl)methyl]-5,5-dimethyl-N-phenyl-, P,2-dioxide; 1,3,2-Dioxaphosphorinane-2-methanamine, N,N-dibutyl-5,5-dimethyl-, 2-oxide; 1,3,2-Dioxaphosphorinane-2-methanimine, N-[(5,5-dimethyl-1,3,2-dioxaphosphorinan-2-yl)methyl]-N-ethyl-5,5-dimethyl-, P, 2-dioxide; 1,3,2-Dioxaphosphorinane-2-methanamine, N-butyl-N-[(5,5-dichloromethyl-1,3,2-dioxaphosphorinan-2-yl)methyl]-5,5-di-chloromethyl-, P,2-dioxide; 1,3,2-Dioxaphosphorinane-2-methanamine, N-[(5,5-di-chloromethyl-1,3,2-dioxaphosphorinan-2-yl)methyl]-5,5 -di-chloromethyl-N-phenyl-, P, 2-dioxide; 1,3,2-Dioxaphosphorinane-2-methanamine, N,N-di-(4-chlorobutyl)-5,5-dimethyl-,2-oxide; 1,3,2-Dioxaphosphorinane-2-methanimine, N-[(5,5-dimethyl-1,3,2-dioxaphosphorinan-2-yl)methyl]-N-(2-chloroethyl)-5,5-di(chloromethyl)-, P,2-dioxide.

The invention also provides a process for the preparation of the novel (1,3,2-dioxaphosphorinanemethan) amine compounds comprising the steps of:

(a) adding phosphorus trichloride to a mixture of a 1,3-diol derivative and water and an organic solvent at a temperature of from about 10° C. to about 60° C. to produce a 5,5-di-substituted 1,3,2-dioxaphosphorinane-2-oxide having the general formula:

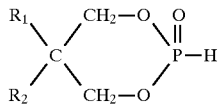

wherein $R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms;

(b) heating the 5,5-di-substituted 1,3,2-dioxaphosphorinane-2-oxide to remove hydrogen chloride, removing excess solvent and purifying the 5,5-di-substituted 1,3,2-dioxaphosphorinane-2-oxide;

(c) reacting the 5,5-di-substituted 1,3,2-dioxaphosphorinane-2-oxide, paraformaldehyde and an amine having the general formula:

$B_Y NH_{3-Y}$, wherein Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms, in an organic solvent to produce a (1,3,2-dioxaphosphorinanemethan) amine compound having the general formula:

$A_{3-Y}$—N—$B_Y$
wherein A is

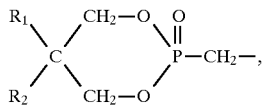

$R_1$ and R2 are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms, Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms; and (d) washing the (1,3,2-dioxaphosphorinanemethan) amine with a base, followed by purifying the (1,3,2-dioxaphosphorinanemethan) amine.

The general reaction sequence for the preparation of the (1,3,2-dioxaphosphorinanemethan) amine compounds of the invention is:

wherein $R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms; and

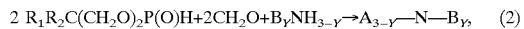

wherein A is

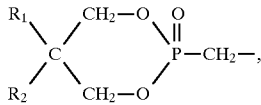

$R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms, Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms. In addition, other elements such as nitrogen, oxygen and sulfur may be present as substituents on the alkyl or aryl groups.

In the first step of the process, phosphorus trichloride was reacted with a 1,3-diol derivative in a mixture of the 1,3-diol derivative and water and a suitable organic solvent at a temperature of from about 10° C. to about 80° C., preferably at a temperature of from about 10° C. to about 60° C., and more preferably at a temperature of about 50° C., to produce an intermediate product, 5,5-di-substituted 1,3,2-dioxaphosphorinane-2-oxide. Suitable 1,3-diol derivatives include, for example, 1,3-propylene glycol, 1,3-isobutylene glycol, neopentyl glycol and halogenated derivatives of these glycols such as, for example, 2,2-bis(chloromethyl)-1,3-propane diol. Suitable organic solvents include benzene, monochlorobenzene, toluene, xylene and similar aromatic compounds which do not react with phosphorus trichloride. In this procedure, the phosphorus trichloride must be added to the slurry below the surface to prevent entrainment losses.

An illustrative example of this reaction provides neopentyl glycol to react with phosphorus trichloride to produce 5,5-dimethyl 1,3,2-dioxaphosphorinane-2-oxide. Another example provides 2,2-bis(chloromethyl)-1,3-propane diol to react with phosphorus trichloride to produce 5,5-di-chloromethyl 1,3,2-dioxaphosphorinane-2-oxide. The 5,5-di-substituted 1,3,2-dioxaphosphorinane-2-oxide was heated to remove hydrogen chloride and vacuum stripping was used to remove excess solvent.

The product, 5,5-di-substituted 1,3,2-dioxaphosphorinane-2-oxide, was purified. The product with lower molecular weight substituents may be distilled at a temperature within the range of from about 100° to about 140° C., preferably at a temperature of about 110° C., at a pressure of from about 0.1 mm. to about 5.0 mm. of mercury and the still bottoms may be recycled to increase yields and reduce waste. During distillation the still bottoms should be maintained at a temperature of approximately 140° C. or less. If the product has higher molecular weight substituents, other purification methods may be used. Air leaks must be minimized, by any known methods, during the distillation as exposure to air and moisture will cause decomposition of the 5,5-di-substituted 1,3,2-dioxaphosphorinane-2-oxide.

In the final step of the process, the 5,5-di-substituted 1,3,2-dioxaphosphorinane-2-oxide produced in the first step of the process was reacted with paraformaldehyde and a primary or secondary amine such as, for example n-butylamine, in an organic solvent to produce a (1,3,2-dioxaphosphorinanemethan) amine compound having the general formula:

$A_{3-Y}$—N—$B_Y$ wherein A is

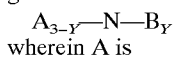
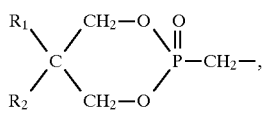

$R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms, Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms. An acid catalyst may be used to facilitate the reaction.

Any suitable organic solvent such as, for example, toluene and xylene may be used. The 1,3,2-dioxaphosphorinane-2-oxide and the amine react at a temperature within the range of from about 10° C. to about 100° C. and the range of from about 40° C. to about 60° C. is preferred.

The (1,3,2-dioxaphosphorinanemethan) amine compound was washed with a base and the material was filtered and purified. High molecular weight compounds may be purified by washing, for example with an alcohol and then with water, before they are dried. Low molecular weight compounds may be purified by distillation.

If the preferred raw materials are used in the process described above, in first step of the process, phosphorus trichloride was reacted with a mixture of 2,2-bis(chloromethyl)-1,3-propane diol and water to produce 5,5-di-chloromethyl 1,3,2-dioxaphosphorinane-2-oxide. In the final step of the process the 5,5-di-chloromethyl 1,3,2-dioxaphosphorinane-2-oxide was reacted with paraformaldehyde and n-butylamine to produce a (1,3,2-dioxaphosphorinanemethan) amine compound having the formula $A_2$—N—$CH_2$—$CH_2$—$CH_2$—$CH_3$ wherein A is

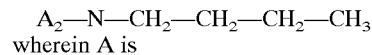
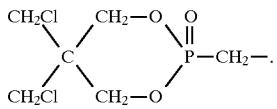

The invention is illustrated by the following examples in which all of the parts and percents are by weight unless otherwise indicated.

EXAMPLE I

Preparation of 5,5-Dimethyl 1,3,2-Dioxaphosphorinane-2-Oxide

A nitrogen purged, glass reaction flask was charged with 226.2 grams of monochlorobenzene, 39 grams of water and 226.2 grams of neopentyl glycol. During a period of about 3 hours, 298.8 grams of phosphorus trichloride were added. During the first one-third of the addition, the reaction is exothermic and the batch was cooled to maintain the temperature between about 40° C. and about 50° C. After about one-third of the phosphorus trichloride was added, hydrogen chloride gas evolved at a substantial rate and external cooling was no longer necessary as the evolution of hydrogen chloride gas is endothermic. The hydrogen chloride gas was sent to a water scrubber. The reactor contents were kept at a temperature between about 40° C. and about 50° C. by heating the reactor and the addition of the phosphorus trichloride was continued at a rate that prevented foaming. After the addition of the phosphorus trichloride was completed, the temperature of the batch was raised to about 110° C. at a rate slow enough to prevent excessive foaming as additional hydrogen chloride gas was eliminated. The batch was held at about 110° C. for about 30 minutes before vacuum stripping was started by gradually reducing the reactor pressure to between about 20 mm. and 25 mm. of mercury. Vacuum stripping was continued until monochlorobenzene ceased to distill under these conditions. The remaining material was then vacuum distilled at a temperature between about 110° C. and about 130° C. and at a pressure between about 0.1 mm. and 2.0 mm. of mercury, with only a small forerun, to yield 300 grams of 5,5-dimethyl 1,3,2-dioxaphosphorinane-2-oxide.

EXAMPLE II

Preparation of a Compound Having the General Formula $A_{3-Y}$—N—$B_Y$

A stirred reactor was charged with 0.30 moles of 5,5-dimethyl 1,3,2-dioxaphosphorinane-2-oxide and 0.15 moles of n-butylamine with toluene as a solvent and 0.30 moles of paraformaldehyde were slowly added at room temperature or below. After the addition was completed, the mixture was slowly heated to about 50° C. until the reaction was complete. The reagents may be added in any order and a small amount of an acid catalyst may be used to facilitate the reaction. The product had the formula:

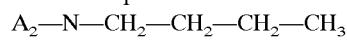

wherein A is $$\begin{array}{c} CH_3 \\ \diagdown \\ CH_3 \end{array} C \begin{array}{c} CH_2-O \\ \diagdown \\ CH_2-O \end{array} P \begin{array}{c} O \\ \diagup \\ \end{array} -CH_2-.$$

While certain preferred embodiments of the invention have been illustrated and described herein, it is to be understood that the invention is not limited thereby and that the invention may be variously practiced within the scope of the following claims.

We claim:

1. A compound having the formula:
$A_{3-Y}$—N—$B_Y$
wherein A is $$\begin{array}{c} R_1 \\ \diagdown \\ R_2 \end{array} C \begin{array}{c} CH_2-O \\ \diagdown \\ CH_2-O \end{array} P \begin{array}{c} O \\ \diagup \\ \end{array} -CH_2-,$$

$R_1$ and $R_2$ are independently selected from the group consisting of hydrogen, halogens, alkyl groups having from 1 to 4 carbon atoms, halogenated alkyl groups having from 1 to 4 carbon atoms, aryl and halogenated aryl groups having from 6 to 8 carbon atoms, Y is 1 or 2 and each B is independently selected from the group consisting of hydrogen, alkyl groups having from 2 to about 8 carbon atoms, halogenated alkyl groups having from 2 to about 8 carbon atoms, aryl and halogenated aryl groups having from 6 to about 8 carbon atoms and wherein the compound is a solid at ambient temperature, and with the proviso that when Y is 2 and B is ethyl that $R_1$ and $R_2$ cannot both be methyl.

2. The compound of claim 1 wherein $R_1$ and $R_2$ are each independently selected from the group consisting of hydrogen, halogens, alkyl groups having from 1 to 4 carbon atoms and halogenated alkyl groups having from 1 to 4 carbon atoms.

3. The compound of claim 2 wherein $R_1$ and $R_2$ are chloromethyl.

4. The compound of claim 1 wherein $R_1$ and $R_2$ are each independently selected from the group consisting of hydrogen, halogens, aryl and halogenated aryl groups having from 6 to 8 carbon atoms.

5. A composition of matter comprising an organic polymeric material and a fire retardant amount of a compound having the formula:
$A_{3-Y}$—N—$B_Y$
wherein A is $$\begin{array}{c} R_1 \\ \diagdown \\ R_2 \end{array} C \begin{array}{c} CH_2-O \\ \diagdown \\ CH_2-O \end{array} P \begin{array}{c} O \\ \diagup \\ \end{array} -CH_2-,$$

$R_1$ and $R_2$ are independently selected from the group consisting of hydrogen, halogens, alkyl groups having from 1 to 4 carbon atoms, halogenated alkyl groups having from 1 to 4 carbon atoms, aryl and halogenated aryl groups having from 6 to 8 carbon atoms, Y is 1 or 2 and each B is independently selected from the group consisting of hydrogen, alkyl groups having from 2 to about 8 carbon atoms, halogenated alkyl groups having from 2 to about 8 carbon atoms, aryl and halogenated aryl groups having from 6 to about 8 carbon atoms and wherein the compound is a solid at ambient temperature, and with the proviso that when Y is 2 and B is ethyl that $R_1$ and $R_2$ cannot both be methyl.

6. The composition of matter of claim 5 wherein the organic polymeric material is selected from the group consisting of polyurethane foams, other polyurethane containing compositions, and compositions containing polyesters, styrenic polymers, polyvinyl chloride, polyvinyl acetates or polycarbonates.

7. The composition of matter of claim 6 wherein the organic polymeric material is a polyurethane foam.

8. The composition of matter of claim 5 wherein $R_1$ and $R_2$ are each independently selected from the group consisting of hydrogen, halogens, aryl and halogenated aryl groups having from 1 to 4 carbon atoms.

9. The composition of matter of claim 8 wherein $R_1$ and $R_2$ are halogenated methyl groups.

10. The composition of matter of claim 5 wherein $R_1$ and $R_2$ are each independently selected from the group consisting of hydrogen, halogens, aryl and halogenated aryl groups having from 6 to 8 carbon atoms.

11. The composition of matter of claim 5 wherein Y is 1 and each B is independently selected from the group consisting of hydrogen, alkyl groups having from 2 to about 8 carbon atoms and halogenated alkyl groups having from 2 to about 8 carbon atoms.

12. The composition of matter of claim 5 comprising a polyurethane foam and a fire retardant amount of a compound having the formula:
$A_{3-Y}$—N—$B_Y$
wherein A is $$\begin{array}{c} CH_3 \\ \diagdown \\ CH_3 \end{array} C \begin{array}{c} CH_2-O \\ \diagdown \\ CH_2-O \end{array} P \begin{array}{c} O \\ \diagup \\ \end{array} -CH_2-,$$

Y is 1 or 2 and each B is independently selected from the group consisting of hydrogen, alkyl groups having 2 to about 8 carbon atoms, halogenated alkyl groups having from 2 to about 8 carbon atoms, aryl and halogenated aryl groups having from 6 to about 8 carbon atoms and wherein the compound is a solid at ambient temperature, and with the proviso that when Y is 2 and B is ethyl that $R_1$ and $R_2$ cannot both be methyl.

13. A process for the production of compounds having the formula:
$A_{3-Y}$—N—$B_Y$
wherein A is $$\begin{array}{c} R_1 \\ \diagdown \\ R_2 \end{array} C \begin{array}{c} CH_2-O \\ \diagdown \\ CH_2-O \end{array} P \begin{array}{c} O \\ \diagup \\ \end{array} -CH_2-,$$

$R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms, Y is 1 or 2 and each B is independently selected from the group consisting of hydrogen, alkyl groups having from 2 to 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms, comprising the steps of:

(a) adding phosphorus trichloride to a mixture of a 1,3-diol derivative and water and an organic solvent at a temperature of from about 10° C. to about 60° C. to produce a 5,5-di-substituted 1,3,2-dioxaphosphorinane-2-oxide having the general formula:

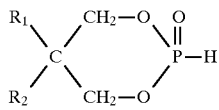

wherein $R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms;

(b) purifying the 5,5-di-substituted 1,3,2-dioxaphosphorinane-2-oxide;

(c) reacting the 5,5-di-substituted 1,3,2-dioxaphosphorinane-2-oxide, paraformaldehyde and an amine having the general formula:

$B_Y NH_{3-Y}$, wherein Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms in an organic solvent to produce a (1,3,2-dioxaphosphorinanemethan) amine compound having the general formula:

$A_{3-Y}$—N—$B_Y$ wherein A is

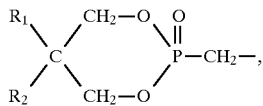

$R_1$ and $R_2$ are independently selected from the group consisting of hydrogen, halogens, alkyl groups having from 1 to 4 carbon atoms, halogenated alkyl groups having from 1 to 4 carbon atoms, aryl and substituted aryl groups having from 6 to 8 carbon atoms and halogenated aryl and halogenated substituted aryl groups having from 6 to 8 carbon atoms, Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms; and (f) purifying and drying the (1,3,2-dioxaphosphorinanemethan) amine compound.

14. A process for the production of compounds having the formula:

$A_{3-Y}$—N—$B_Y$ wherein A is

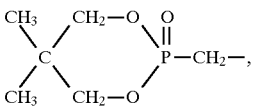

Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms comprising the steps of:

(a) adding phosphorus trichloride to a mixture of neopentyl glycol and water and an organic solvent at a temperature of from about 10° C. to about 60° C. to produce a 5,5-dimethyl 1,3,2-dioxaphosphorinane-2-oxide having the general formula:

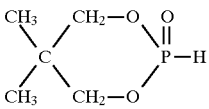

(b) purifying the 5,5-dimethyl 1,3,2-dioxaphosphorinane-2-oxide;

(c) reacting the 5,5-dimethyl 1,3,2-dioxaphosphorinane-2-oxide, paraformaldehyde and an amine having the general formula $B_Y NH_{3-Y}$, wherein Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and halogenated substituted aryl groups having from 6 to about 8 carbon atoms, in an organic solvent with an acid catalyst to produce a (1,3,2-dioxaphosphorinanemethan) amine compound having the general formula:

$A_{3-Y}$—N—$B_Y$ wherein A is

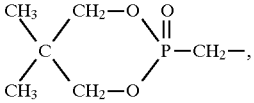

Y is 1 or 2 and each B is independently selected from the group consisting of hydrogen, alkyl groups having from 2 to about 8 carbon atoms, halogenated alkyl groups having from 2 to about 8 carbon atoms, aryl and substituted aryl groups having from 6 to about 8 carbon atoms and halogenated aryl and substituted aryl groups having from 6 to about 8 carbon atoms; and (d) purifying and drying the (1,3,2-dioxaphosphorinanemethan) amine compound.

15. The composition of claim 1 wherein Y is 1.

16. The composition of claim 5 wherein Y is 1.

* * * * *